United States Patent [19]

Saccomano

[11] Patent Number: 5,395,935
[45] Date of Patent: Mar. 7, 1995

[54] ENDO-BICYCLO[2.2.1]HEPTAN-2-OL AND DERIVED PHARMACEUTICAL AGENTS

[75] Inventor: Nicholas A. Saccomano, Ledyard, Conn.

[73] Assignee: Pfizer Inc., New York, N.Y.

[21] Appl. No.: 135,208

[22] Filed: Oct. 12, 1993

Related U.S. Application Data

[60] Division of Ser. No. 855,047, May 8, 1992, Pat. No. 5,270,206, and a continuation-in-part of Ser. No. 155,932, Nov. 19, 1988, abandoned.

[51] Int. Cl.⁶ ............................................. C07D 239/36
[52] U.S. Cl. ..................................................... 544/318
[58] Field of Search ........................................ 544/318

[56] References Cited

U.S. PATENT DOCUMENTS

| | | | |
|---|---|---|---|
| 3,636,039 | 1/1972 | Gruenman et al. | 260/309.7 |
| 3,772,288 | 11/1973 | Hardtmann et al. | 260/251 R |
| 3,843,712 | 10/1974 | Axen | 260/468 G |
| 3,850,922 | 11/1974 | Matuo et al. | 260/247.2 A |
| 3,920,673 | 11/1975 | Kelly | 260/307 F |
| 3,923,833 | 12/1975 | Gruenman et al. | 260/340.5 |

(List continued on next page.)

FOREIGN PATENT DOCUMENTS

| | | |
|---|---|---|
| 0134928 | 3/1985 | European Pat. Off. . |
| 1451154 | 7/1966 | France . |
| 3315797 | 10/1984 | Germany . |
| 8706576 | 11/1987 | WIPO . |
| 9115451 | 10/1991 | WIPO . |

OTHER PUBLICATIONS

Brown, Herbert C. et al., "Hydraboration. 61. Diisopinocampheylborane of High Optical Purity, Improved Preparation and Asymmetric Hydroboration of Representative Cis–Disubstituted Alkenes," *J. Org. Chem.*, 47, pp. 5065–5069 (1982).

(List continued on next page.)

*Primary Examiner*—John M. Ford
*Attorney, Agent, or Firm*—Peter C. Richardson; Paul H. Ginsburg; Garth C. Butterfield

[57] ABSTRACT

An optically active compound selected from the group consisting of a compound having the absolute stereochemical formula

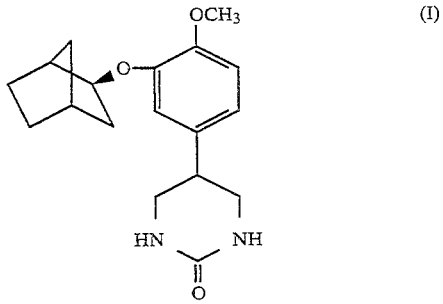

(I)

and a compound having the absolute stereochemical formula

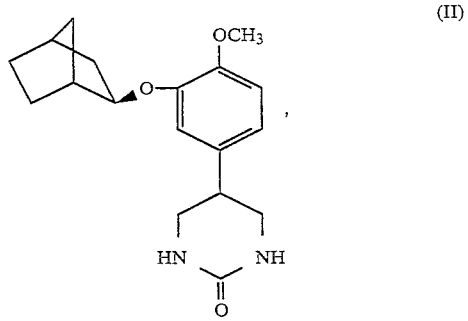

(II)

and intermediates thereof.

2 Claims, No Drawings

U.S. PATENT DOCUMENTS

| | | | |
|---|---|---|---|
| 4,006,243 | 2/1977 | Strehlke et al. | 424/273 |
| 4,012,495 | 3/1977 | Schmiechen et al. | 424/274 |
| 4,122,273 | 10/1978 | Buchanan et al. | 544/355 |
| 4,123,440 | 10/1978 | Buchanan et al. | 260/326.28 |
| 4,153,713 | 5/1979 | Huth | 424/274 |
| 4,181,674 | 1/1980 | Newton et al. | 260/448.8 R |
| 4,193,926 | 3/1980 | Schmiechen | 260/326.5 S |
| 4,261,995 | 4/1981 | Weinhardt et al. | 424/251 |
| 4,308,278 | 12/1981 | Schneider | 424/273 |
| 4,567,263 | 1/1986 | Eicken | 544/263 |
| 4,582,834 | 4/1986 | Stenzel | 514/274 |
| 4,732,853 | 3/1988 | Whitesides et al. | 435/123 |
| 4,837,207 | 6/1989 | Trivedi | 514/46 |
| 4,857,651 | 8/1989 | Brown et al. | 549/443 |
| 4,861,891 | 8/1989 | Saccomano et al. | 546/194 |
| 4,962,223 | 10/1990 | Cannata et al. | 558/408 |
| 5,128,358 | 7/1992 | Saccomano et al. | 514/392 |
| 5,196,426 | 3/1993 | Saccomano et al. | 514/258 |

OTHER PUBLICATIONS

Irwin, Anthony J. et al., "Enzymes in Organic Synthesis, Influence of Substrate Structure on Rates of Horse Liver Alcohol Dehydrogenase-catalysed Oxidoreductions," *J. C. S. Perkin I*, pp. 1636–1642 (1978).

Irwin, Anthony J. et al., "Stereoselective Horse Liver Alcohol Dehydrogenase Catalyzed Oxidoreductions of Some Bicyclic[2.2.1]and [3.2.1]Ketones and Alcohols," *J. Am. Chem. Soc.*, 98, pp. 8476–8432 (1976).

Kirchner, Geald et al., "Resolution of Racemic Mixtures via Lipase Catalysis in Organic Solvents," *J. Am. Chem. Soc.*, 107, pp. 7072-7076 (1985).

Nakazaki, Massao et al., "Microbial Stereodifferentiating Reduction of Carbonyl Compounds; Proposed Quadrant Rule," *J. Org. Chem.*, 45, pp. 4432–4440 (1980).

Oberhauser, Th. et al., "Enzymatic Resolution of Norbornane-Type Esters," *Tetrahedron*, 43, No. 17, pp. 3931 to 3944 (1987).

Saccomano, Nicholas A. et al., "Calcium-Independent Phosphodiesterase Inhibitors as Putative Antidepressants: [3-(Bicycloalkyloxy)-4-methoxypphenyl-]-2-imidazolidinones," *J. Med. Chem.*, 34, pp. 291–298 (1991).

Saccomano, Nicholas A. et al., "Preparation of N-heterocyclic compounds as calcium-independent cAMP phosphodiesterase inhibitor antidepressants," *Chemical Absracts*, p. 694, No. 109:129006e (1988).

ENDO-BICYCLO[2.2.1]HEPTAN-2-OL AND DERIVED PHARMACEUTICAL AGENTS

This patent application is a divisional of U.S. patent application Ser. No. 07/855,047, filed May 8, 1992, now U.S. Pat. No. 5,270,206, and this patent application is a continuation-in-part of U.S. patent application Ser. No. 07/155,932, filed Jan. 19, 1988, now abandoned.

BACKGROUND OF THE INVENTION

The present invention is directed to a process for the preparation of (+)-(2R)-endo-norborneol and (−)-(2S)-endo-norborneol, and for their further conversion, respectively, to the pharmaceutical agents 5- ( 3 -[(2S) -exo-bicyco[2.2.1 ]hept- 2-yloxy ]-4 -methoxy-phenyl) -3,4,5,6-tetrahydropyrimidin-2(1H) -one, of the formula

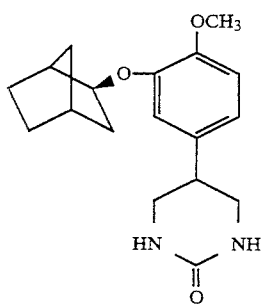

and its enantomer, 5-(3-[2R) -exo-bicyclo[2.2.1]hept-2-yloxy]-4-methoxyphenyl)-3,4,5,6-tetrahydropyrimidin-2(1H)-one, of the formula

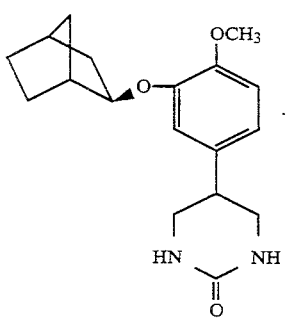

The present invention is also directed to these particular optically active pharmaceutical agents per se, and to intermediates [of the formulas (III) to (VI) below] used in their synthesis.

(2R)-endo-Norborneol is alternatively named (2R)-endo-bicyclo[2.2.1]heptan-2-ol or (1S,2R,4R)bicyclo[2.2.1]heptan-2-ol. Likewise, enantiomeric (2S)-endo-norborneol is alternatively named (2S)-endobicyclo [2.2.1 ]heptan-2-ol or ( 1R, 2S, 4S) -bicyclo [2.2.1 ]-heptan-2-ol. Analogously, derived ( 2S ) -exo-bicyclo[2.2.1 ]hept-2-yl and (2R) -exo-bicyclo [2.2.1 ]hept- 2-yl substituent groups are alternatively named, respectively, (1S,2S,4R)-bicyclo[2.2.1]hept-2-yl and ( 1R, 2R, 4S) -bicyclo [2.2.1 ]hept-2-yl.

The present compounds of the formulas (I) and (II) represent particularly valuable species of the compounds broadly disclosed by Saccomano, et al. in published International Patent Application W087/06576, having utility as antidepressants. Although that reference specifically discloses racemic 5-(3-exo-bicyclo [2.2.1 ]hept-2-yloxy]-4-methoxyphenyl)- 3,4,5,6-tetrahydropyrimidin-2 (1H) -one, there is no specific disclosure of the present optically active variants thereof, or of any specific method for their preparation.

Heretofore, optically active (2R)-and (2S)-endo-norborneols were obtained by resolution of racemic exo-norborneol hemiphthalate ester with optically active phenethylamines, hydrolysis to optically active exo-norborneols, $CrO_3$ oxidation to optically active norbornanones and finally $Li(s-Bu)_3BH$ reduction to the desired endo-isomers. Irwin et al., J. Am. Chem. Soc., v. 98, pp. 8476–8481 (1979). According to the same reference, enantiomeric enrichment of endo-norborneols was achieved by incomplete horse liver alcohol dehydrogenase catalyzed reduction of racemic 2-norbornanone; while incomplete oxidation of racemic exo-norborneol catalyzed by the same enzyme gave enantiomerically enriched exo-norborneols. (−)-exo-Norborneol has also been prepared from norbornene by asymmetric hydroboration, Brown, et al., J. Org. Chem, v. 47, pp. 5065–5069 (1982).

Heretofore, certain chiral alcohols have been resolved using transesterification catalyzed by porcine pancreatic lipase in a nearly anhydrous organic solvent. Kirchner, et al., J. Am. Chem. Soc. v. 107, pp. 7072–7076 (1985). For example, 47% conversion of racemic 2-octanol and 2,2,2-trichloroethyl butyrate gave (R)-2-octyl butyrate of high optical purity. However, when this method was applied to racemic exo-norborneol, both the recovered alcohol and the product butyrate ester remained essentially racemic, even though the transesterification was definitely enzyme mediated (as shown by lack of reaction absent the enzyme).

SUMMARY OF THE INVENTION

In spite of the fact that lipase catalyzed transesterification of exo-norborneol does not provide a viable method for the optical resolution of the exo-isomer, we persisted and discovered this process to be a simple and efficient method for the optical resolution of said endo-norborneol. Thus, in one of its aspects, the present invention is directed to a process-for the preparation of optically active endo-bicyclo[2.2.1]heptan-2-ols (endo-norborneols) which comprises the steps of:
  (a) partial transesterification between racemic endo-bicyclo[2.2.1]heptan-2-ol and 2,2,2-trichloroethyl butyrate in a substantially anhydrous, reaction inert organic solvent in the presence of a mammalian pancreatic lipase;
  (b) separation, from the resulting mixture, of unreacted (−)-(2S)-endo-bicyclo[2.2.1]heptan-2-ol [(2S)-endo-norborneol] of the formula

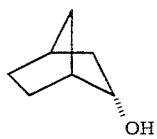

and of (2R)-endo-bicyclo[2.2.1]hept-2-yl butyrate, an ester which is hydrolyzed to form enantiomeric (+)-(2R)-endo-bicyclo[2.2.1]heptan-2-ol [(2R)-endo-norborneol] of the formula

As used above, and elsewhere herein, the expression "reaction inert solvent" refers to a solvent which does not interact with starting materials, reagents, intermediates or products in a manner which adversely affects the yield of the desired product or products.

In preferred embodiments of this process, the enzyme is of porcine origin, the solvent is ether, and the resulting optically active (2R)- and (2S)-endobicyclo [2.2.1 ]heptan-2 -ols are further reacted with 3-hydroxy-4-methoxybenzaldehyde in the presence of triphenylphosphine and diethyl azadicarboxylate to form, respectively, optically active aldehydes 3-( (2S)-exo-bicyclo [2.2.1 ]hept-2-yloxy) -4-methoxybenzaldehyde, of the formula

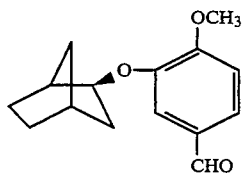

and 3- ((2R) -exo-bicyclo [2.2.1 ]hept-2-yloxy) -4-methoxybenzaldehyde, of the formula

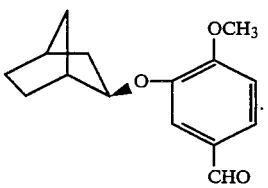

These in turn are further converted to the compounds of the formula (I) and (II), via the steps and intermediates as follows:

(a) reaction of the optically active 3- (exo-bicyclo [2.2.1 ]hept-2-yloxy) -4-methoxybenzaldehyde (III) or (IV) with at least 2-molar equivalents of 2-cyanoacetic acid in pyridine in the presence of a catalytic amount of piperidine at a temperature in the range of about 25°–100° C. to produce an optically active 3- (3- (exo-bicyclo [2.2.1 ]hept-2-yloxy) -4-methoxyphenyl) pentanedinitrile, of the formula (V) or (VI) below wherein Y is CN;

(b) conventional hydration of said pentanedinitrile to produce an optically active 3- (3- (exo-bicyclo [2.2.1 ]hept-2-yloxy) -4-methoxyphenyl ) glutaramide, of the formula (V) or (VI) below wherein Y is $CONH_2$; and (c) cyclization of said glutaramide by the action of a molar excess of lead tetraacetate in pyridine to form an optically active 5- (3-(exo-bicyclo [2.2.1 ]hept-2-yloxy)-4-methoxyphenyl) -3,4,5,6-tetrahydropyrimidin2(1H)-one of the formula (I) or (II) above.

The present invention is also directed to the heretofore unavailable optically active compound species of the formulas (I) and (II) above, and to optically active intermediates of the formulas

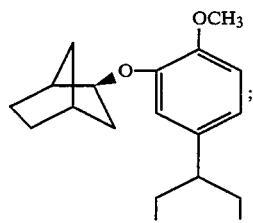

and

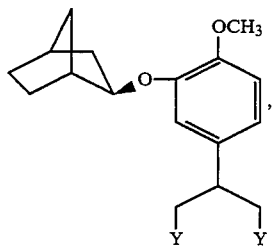

wherein Y is —CN or —$CONH_2$.

DETAILED DESCRIPTION OF THE INVENTION

The various aspects of the present invention are readily carried out. Accordingly, racemic endo-norborneol and 2,2,2-trichloroethyl butyrate ester, in substantially molar equivalents, are dissolved in a reaction inert, organic solvent. The preferred solvents in the present case are ethers such as ether itself, diisopropyl ether, tetrahydrofuran or dioxane, which are substantially anhydrous and at the same time, readily dissolve the indicated reactants. Mammalian pancreatic lipase (preferably porcine pancreatic lipase which is readily available from commercial sources) is added in portions as a dry powder, in amounts as needed to maintain a reasonable rate of transesterification. Temperature, which is quite critical, will generally be in the range of about 15°–40° C. If the temperature is too low, the rate will be too slow, while temperatures which are too high will rapidly inactivate the enzyme. The reaction is followed analytically (conveniently by $^1$H-NMR by which the starting materials and ester product are readily differentiated) and terminated when the reaction is about 40–50% complete, so as to maximize the optical purity of recovered (2S)-endo-norborneol and (2R)-endo-norbornyl butyrate. These products are separated by conventional methods, conveniently by chromotographic methods, and the ester hydrolyzed by conventional methods well known in the art to yield (2R)-endo-norborneol.

According to the present invention, the resulting optically active (2R)- and (2S)-endo-norborneols are converted, respectively, to the aldehydes of above formulas (III) and (IV) according to the method disclosed in WO87/06576 cited and summarized above.

Further, according to the present invention, the aldehydes of the above formulas (III) or (IV) are condensed with at least two molar equivalents of cyanoacetic acid to-yield a dinitrile of the formula (V) or (VI), wherein Y is CN. Conveniently, this condensation is carried out in pyridine, which also serves in part as a basic catalyst, in the presence of a secondary amine, preferably unhindered such as piperidine or pyrrolidine, in an amount which is generally a molar excess. Although the initial stages of the reaction may be carried out at ambient temperature, the reaction (including decarboxylation) is best completed by heating at a temperature in the range of about 80°–110° C.

The dinitriles of the formula (V) or (VI) are then hydrated to the bis-amides of the formula (V) or (VI), wherein Y is $CONH_2$, by conventional methods. Conveniently, this is accomplished by reacting the dinitrile in a reaction inert aqueous organic solvent (e.g., 2:1 actone: $H_2O$) with a half-molar quantity of $H_2O_2$ in the presence of excess $Na_2CO_3$ at a temperature in the range of about 0°–30° C.

Finally, the bis-amides of the formula (VI) are cyclyzed to form an optically active 5-(3-(exo-bicyclo[2.2.1]hept-2-yloxy) -4-methoxyphenyl) -3,4,5,6-tetrahydropyrimidin-2(1H)-one of the formula (I) or (II). This is best accomplished by means of a molar excess of lead tetraacetate in excess pyridine as solvent. Temperature is not critical, with temperatures in the range of 0°–60° C. generally proving satisfactory. Conveniently, ambient temperatures are employed, avoiding the cost of heating or cooling.

As noted at page 25 of patent application WO87/06576, cited above, 5-(3-(exo-bicyclo[2.2.1]hept-2-yloxy) -4-methoxyphenyl) -3,4,5,6-tetrahydropyrimidin-2(1H)-one possesses in vitro activity as an inhibitor of phosphodiesterases prepared from cerebral cortices of rats. More pertinent to its utility in the treatment of asthma is its activity as an inhibitor of phosphodiesterases derived from guinea pig lung, as detailed below in Example 1, where present optically active compounds of the formulas (I) and (II) show like activity. Utility in the treatment of asthma is further reflected by the ability of the present compounds to inhibit in vivo eosinophil migration into sensitized lung tissue in antigen challenged guinea pigs, as detailed in Example 2. Utility of the present compounds in psoriasis and dermatitis due to contact hypersensitivity is reflected by the ability of the present compounds to inhibit in vivo skin edema in guinea pigs sensitized to ovalbumin, as detailed in Example 3.

In the systemic treatment of asthma or inflammatory skin diseases with a compound of the formula (I) or (II), or with the corresponding racemic compound, the dosage is generally from about 0.01 to 2 mg/kg/day (0.5–100 mg/day in a typical human weighing 50 kg) in single or divided doses, regardless of the route of administration. Of course, depending upon the exact compound and the exact nature of the individual illness, doses outside this range will be prescribed at the discretion of the attending physician. In the treatment of asthma, intranasal (drops or spray), inhalation of an aerosol through the mouth, and conventional oral administration are generally preferred. However, if the patient is unable to swallow, or oral absorption is otherwise impaired, the preferred systemic route of administration will be parenteral (i.m., i.v.). In the treatment of inflammatory skin diseases, the preferred route of administration is oral or topical. In the treatment of inflammatory airway diseases, the preferred route of administration is intranasal or oral.

The compounds of the present invention are generally administered in the form of pharmaceutical compositions comprising one of said compounds together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; for topical administration, in the form of solutions, lotions, ointments, salves and the like, in general containing from about 0.1 to 1% (w/v) of the active ingredient; and for intranasal or inhaler administration, generally as a 0.1 to 1% (w/v) solution.

The present invention is illustrated by the following examples, but is not limited to the details thereof.

EXAMPLE 1

Inhibition of Pulmonary Phosphodiesterase (PDEIV)

Lung tissue from guinea pigs was placed in a homogenization buffer solution (20 mM Bistris, 5 mM 2-mercaptoethanol, 2 mM benzamidine, 2 mM EDTA, 50 mM sodium acetate, pH 6.5) at a concentration of 10 ml/gm of tissue. The tissue was homogenized using a Tekmar Tissumizer at full speed for 10 seconds. Phenylmethylsulfonyl fluoride (PMSF, 50 mM in 2-propanol) was added to the buffer immediately prior to homogenization to give a final PMSF concentration of 50 $\mu$M. The homogenate was centrifuged at 12,000×g for 10 minutes at 4° C. The supernatant was filtered through gauze and glass wool and then applied to a 17×1.5 cm column of DEAE-Sepharose CL-6B, pre-equilibrated with homogenization buffer, at 4° C. A flow rate of 1 ml/min was used. After the supernatant had passed through the column, the column is washed with a volume of homogenization buffer at least two times that of the supernatant. PDE was eluted with a linear gradient of 0.05–0.1M sodium acetate. One hundred×5 ml fractions were collected. Fractions were saved based on specific PDEIV activity, determined by [3H]cAMP hydrolysis and the ability of a known PDEIV.

Preparation of test compounds—Compounds were dissolved in DMSO at a concentration of $10^{-2}$M, then diluted 1:25 in water ($4\times10^{-4}$M compound, 4% DMSO). Further serial dilutions are made in 4% DMSO to achieve desired concentrations. Final DMSO concentration in assay tubes was 1%.

In triplicate, the following were added to a 12×75 mm glass tube, in order, at 0° C.: (all concentrations are given as final concentrations in assay tube)

25 $\mu$l compound or DMSO (1%, for control and blank)
25 $\mu$l assay buffer (50mM Tris, 10 mM $MgCl_2$, pH 7.5)
25 $\mu$l [3H]-cAMP (1 $\mu$M)
25 $\mu$l PDEIV enzyme ( for blank, enzyme is preincubated in boiling water bath for 10 minutes.

The reaction tubes were shaken and placed in a water bath (37° C.) for 10 minutes, at which time the reaction was stopped by placing the tubes in a boiling water bath for 2 minutes. Washing buffer (0.5 ml, 0.1M HEPES/0.1M NaCl, pH 8.5) was added to each tube in an ice bath. The contents of each tube were applied to an Affi-Gel 601 column (boronate affinity gel, 1.2 ml bed Volume) previously equilibrated with washing buffer. [3]cAMP was washed with 2×6 ml washing buffer, and [3H]5'AMP was then eluted with 6 ml 0.25M acetic acid. After vortexing, 1 ml of the elution was added to 3 ml Atomlight scintillation fluid in an appropriate vial, vortexed, and counted for [3H ].

Percent inhibition is determined by the formula:

$$\% \text{ inh} = 1 - \frac{\text{avg. cpm (test compound)} - \text{avg. cpm (blank (boiled enzyme))}}{\text{avg. cpm (control (no compound))} - \text{avg. cpm (blank (boiled enzyme))}}$$

IC50 is defined as that concentration of compound which inhibits 50% of specific hydrolysis of [3H]cAMP to [3H]5′AMP.

In this test, racemic 5-(3-(exo-bicyclo[2.2.1]-hept-2-yloxy)-4-methoxyphenyl)-3,4,5,6-tetrahydropyrimidin-2(1H)-one demonstrated an $IC_{50}$ of 0.5 μM. In this test, substantially the same degree of activity was seen with each of the two corresponding optically active, enantiomeric compounds.

EXAMPLE 2

Inhibition of Eosinophil Migration into Sensitized Lung Tissue Challenged with Antigen in Guinea Pigs Normal Hartley guinea pigs (300–350 grams) delivered from Charles River Laboratories were housed 5–7 days before sensitization. Guinea pigs were then sensitized with 0.5 mg/kg anti-OA IgG1 or saline as control. After 48–72 hours, guinea pigs were dosed P.O. in groups of six animals each with compounds at up to 32 mg/kg using 2% Tween 80 as vehicle. After 1–1.5 hours the animals were injected i.p. with 5 mg/kg pyrilamine. Thirty minutes following pyrilamine administration, animals were exposed to 10 minutes of a 0.1% ovalbumin (OA) aerosol followed by a 15 minute cloud decay period in a Tri-R Airborne Infection Apparatus (Compression air flow=20 L/min, main air flow=8.4 L/min). Guinea pigs were removed from the apparatus and caged for 18 hours prior to sacrifice and the following lung lavage procedure.

The guinea pigs were killed with 3 ml urethane (0.5 g/ml) and the trachea was separated from the surrounding tissue. Surgical string was tied loosely around the trachea and an incision was made in the trachea about 1–2 cm from the thymus gland. A blunt, 15G, 1 cm feeding needle was inserted into the trachea and the string was tightened to secure the needle in place. Three × 10 ml saline was lavaged in the lungs five times. Approximately 20–25 ml was recovered and placed in a 50 ml conical tube on ice. Lavage fluid (0.475 ml) was aliquoted in a polystyrene tube containing 0,025 ml 2% Triton X-100 detergent (in duplicate).

The aliquoted sample with Triton was diluted with 1 ml PBS/0.1% Triton buffer (pH 7.0). The diluted sample (0,025 ml) was aliquoted and an additional 0.125 ml of PBS/0.1% Triton buffer was added. A colorimetric reaction was begun by adding 0.300 ml of 0.9 mg/ml o-phenylenediamine dihydrochloride (OPD) in 50 mM Tris buffer/0.1% Triton (pH 8.0) plus 1 μl/ml hydrogen peroxide. After 5 minutes of incubation, 0.250 ml 4M sulfuric acid-Has added to stop the reaction. The O.D. of the mixture was measured at 490 nm, with background O.D. (blank tube) subtracted out.

Duplicate O.D. readings were averaged to obtain a single value for each animal. Average O.D. +/− standard error is calculated using the six obtained values within each group of animals. Specific EPO response due to antigen challenge is calculated by:

1000×[Avg O.D. (sens., challenged)−Avg. O.D. (non-sens., challenged)]

Percent inhibition of specific EPO response due to drug pretreatment is calculated by:

$$\frac{\text{Avg O.D. (sens., drug-treated, challenged)} - \text{Avg O.D. (non-sens., challenged)}}{\text{Avg O.D. (sens., challenged)} - \text{Avg O.D. (non-sens., challenged)}} \times 100\%$$

In this test, the racemic 5-(3-(exo-bicyclo[2.2.1.]hept-2-yloxy)-4-methoxy-3,4,5,6-tetrahydropyrimidin-2(1H)-one demonstrated an ED50 of 10 mg/kg.

EXAMPLE 3

Inhibition of Skin Edema in Guinea Pigs Sensitized to Ovalbumin

Four guinea pigs (Hartley, male, 350–400 g) were sensitized with anti-ovalbumin IgG1 antibody. Two guinea pigs were orally dosed with 32 mg/Kg of the test compound and two other guinea pigs were dosed with vehicle (2% Tween-80). One-hour after dosing, each guinea pig was injected intraveneously with 1 ml of Evan Blue (7 mg/ml) and then his skin was challenged intradermally with 0.1 ml of ovalbumin (0.1%) or PBS. Twenty minutes after challenge, the skin was removed and skin edematous site (circular blue spots at challenge sites) was examined visually.

Ovalbumin challenge resulted in edematous formation at the skin site challenged with ovalbumin whereas PBS challenge showed little skin edema. Both intensity and area of blue spots at antigen-challenged sites were markedly reduced in two guinea pigs dosed with racemic 5-(3-exo-bicyclo[2.2.1]hept-2-yloxy)-4-methxoyphenyl) -3,4,5,6-tetrahydropyrimidin-2 (1H) -one as compared to the edema in vehicle-dosed animals.

This result demonstrates that this compound is effective against antigen-induced skin edema in guinea pigs.

EXAMPLE 4

(+)-(2R)- and (−)-(2S)-endo-Norborneol [(2R)- and (2S)-endo-Bicyclo[2.2.1]heptan-2-ol]

dl-Endonorborneol, (5.0 g, 44.6 mmol) and trichloroethyl butyrate, (5.1 g, 23.2 mmol) were dissolved in 40 ml of diethyl ether. 4A molecular sieves (4 g) were added and the mixture was stirred at room temperature. Porcine pancreatic lipase (Sigma, Type II, crude) was added portionwise in the amounts of 0.5 g, 1.0 g, 1.0 g, 1.0 g and 0.5 g at times 0, 20, 43, 50 and 67 hours, respectively. The reaction was monitored via $^1$HNMR and at approximately 50% completion. (92h) filtered through diatomaceous earth and evaporated in vacuo without heat. (The alcohol sublimes easily). The crude residue was flash chromatographed on silica with a gradient eluent system of 2–25% ether/hexane to afford 2.9 g (15.9 mmol) of (2R)-endonorbornyl butyrate as a clear oil and 1.8 g (16.0 mmol) of (2S)-endonorborneol as a white solid; [alpha]$_D$= −2.03°; e.e. 87.2% (by $^1$HNMR of derived (S) -alpha-methoxy-alpha- (trifluoromethyl) phenylacetic acid (MTPA) ester. Because the specific rotation is so small, the e.e. values determined by NMR are a much more reliable measure of optical purity.

The recovered endonorbornyl butyrate (2.3 g, 12.6 mmole), $K_2CO_3$ (2.5 g, 18.0 mmol) and methanol (65 ml) were stirred at room temperature for 64 hours before being partitioned between diethyl ether and water. The organic portion was washed with water and brine, dried ($Na_2SO_4$), filtered and concentrated in vacuo to afford 1.3 g (11.6 mmol, 91.9% yield) of (2R)-endonorborneol; [alpha]$_D$= +2.7°; e.e. 87.6% (based on $^1$HNMR of MTPA ester).

These process steps were repeated with ester exchange carried only to 44% completion to yield (2S)-endonorborneol of lower optical purity in greater than 90% yield; [alpha]$_D$= −0.88; e.e. 71.4 (based on $^1$HNMR, as above); and (2R)-endonorborneol of higher optical purity in 56.4% yield; e.e. greater than 95% (based on $^1$HNMR as above).

EXAMPLE 5

3-[(2S)-exo-Bicyclo [2.2.1]hept-2-yloxy]-4-methoxybenzaldehyde

Diethylazodicarboxylate (28.5 g, 27.7 ml, 0.141 mol) and triphenylphosphine (36.9 g, 0.141 tool) were dissolved in 200 ml of tetrahydrofuran. To this solution was added (+)-(2R)-endo-norboreol (7.9 g., 0.0705 mol) in 100 ml of tetrahydrofuran, followed by 3-hydroxy-4-methoxybenzaldehyde (isovanillin; 21.4 g, 0.141 mol) in 100 ml of tetrahydrofuran. The resulting mixture was heated at reflux for two days, then cooled, diluted with 1.5 liters of ether, washed in sequence with half volumes of water (2x), 0.5N NaOH (2x), water and brine; dried (Na$_2$SO$_4$), stripped and the residue chromatographed on silica gel gradiently eluting with 0 to 10% ethyl acetate to yield 8.5 g of present title product, 8.5 g (49%), [alpha]$_D$= +24.5° (deuterochloroform).

By the same method, (−)-(2S)-endo-norborneol was converted to 3-[(2R)-exo-bicyclo [2.2.1]hept-2-yloxy]-4-methoxybenzaldehyde, identical in physical properties, except for sign of rotation.

EXAMPLE 6

3-(3-[(2S)-exo-Bicyclo[2.2.1]hept-2-yloxy]4-methoxyphenyl)pentanedinitrile

Title product of the preceding Example (8.5 g, 0.0346 tool) was dissolved in 250 ml of pyridines. Cyanoacetic acid (14.6 g, 0.171 tool) and piperidine (5 ml) were added and the mixture stirred at room temperature for 4 hours, then at 60° C. for 2 hours and finally at 100° C. for 24 hours. Solvent was removed by stripping in vacuo and the residue was taken up in 250 ml ethyl acetate, washed with saturated NaHCO$_3$ and then water, restripped and crystallized from isopropyl alcohol/isopropyl ether to yield 5.84 g (54%) of present title product; m.p. 121°-123° C.; [alpha]$_D$= +17.8° (deuterochloroform).

By the same method, the entiomeric product of the preceding Example was converted to 3-(3-[(2R)-exobicyclo [2.2.1]hept-2-yloxy]-4-methoxyphenyl)-pentanedinitrile, having identical physical properties except for sign of rotation.

EXAMPLE 7

3-(3-[(2S)-exo-Bicyclo[2.2.1]hept-2-yloxy]4-methoxyphenyl)glutaramide

To title product of the preceding Example (5.82 g, 0.018 mol) in 150 ml of 2:1 acetone:H$_2$O by volume was added 5 ml 10% Na$_2$CO$_3$ followed by the dropwise addition of 30% H$_2$O$_2$ (8 ml, 0.094 mol) maintaining a temperature of 0°-5° C. After stirring for 16 hours at room temperature, the mixture was poured into water (300 ml) and ethyl acetate (500 ml) and the mixture stirred for 1 hour to dissolve all solids. The organic layer was separated, washed with H$_2$O and the brine, dried and stripped to a crystalline residue which was flash chromatographed on silica gel using 15:1 CH$_2$Cl$_2$:CH$_3$OH as eluant to yield 3.7 g of present title product, m.p. 198.5°-199.5° C.; ir (KBr) cm$^{-1}$ 3335, 3177, 2952, 1674, 1631, 1516, 1406, 1256, 1142, 1003, 809, 685, 641 cm$^{-1}$.

By the same method, the enantiomeric product of the preceding Example was converted to 3-(3-[(2R)-exobicyclo [2.2.1]hept-2-yloxy]-4-methoxyphenyl)-glutaramide, having the same physical properties, except for sign of rotation.

EXAMPLE 8

5-(3-[(2S)-exo-Bicyclo[2.2.1.]hept-2-yloxy]-4methoxyphenyl)-3,4,5,6-tetrahydropyrimidin-2 (1H)-one To title product of the preceding Example (3.7 g, 0.0107 mol was dissolved in 250 ml of pyridine was added lead tetraacetate (10.92 g, 0.0246 tool) in 250 ml of pyridine. After stirring for 30 hours, the reaction was stripped in vacuo, and the oily residue taken up in 100 ml CH$_2$C$_2$, washed with H$_2$O and the brine, dried (Na$_2$SO$_4$), stripped, and the resulting solids triturated with ether to yield present title product as a white solid, 1.21 g; m.p. 202°-203° C.; [alpha]$_D$= +14.45° (deuterochloroform).

By the same method, the enantiomeric product of the preceding Example was converted to 5-(3-(2R)-exobicyclo [2.2.1]hept-2-yloxy]-4-methoxyphenyl)-3,4,5,6-tetrahydropyrimidin-2(1H)-one, having the same physical properties except for sign of rotation.

I claim:

1. An enantiomerically pure compound having the absolute stereochemical formula

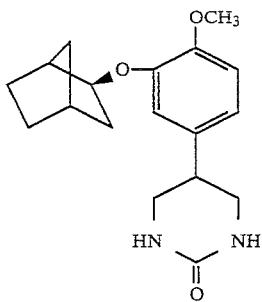

substantially free of the (−) enantiomer.

2. An enantiomerically pure compound having the absolute stereochemical formula

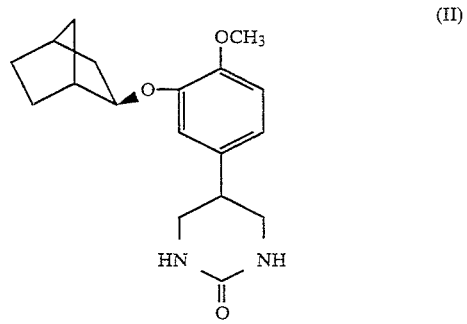

substantially free of the (+) enantiomer.

* * * * *